United States Patent [19]

Bryant et al.

[11] Patent Number: 5,798,699
[45] Date of Patent: *Aug. 25, 1998

[54] METHOD FOR MONITORING AND SELECTIVELY SAMPLING A FLUID FLOW STREAM

[75] Inventors: Robert L. Bryant, DeKalb County; Charles R. Veal, Gwinnett County, both of Ga.

[73] Assignee: Chemtrac Systems, Inc., Norcross, Ga.

[*] Notice: The term of this patent shall not extend beyond the expiration date of Pat. No. 5,578,995.

[21] Appl. No.: 779,051

[22] Filed: Jan. 6, 1997

[51] Int. Cl.$^6$ .................................................. G08B 21/00
[52] U.S. Cl. ............... 340/627; 340/309.15; 250/338.1; 250/339.11
[58] Field of Search ............................ 340/627, 309.15; 250/573, 574; 356/37, 338, 339, 442

[56] References Cited

U.S. PATENT DOCUMENTS

| | | | |
|---|---|---|---|
| 3,845,480 | 10/1974 | Steinberg | 340/627 |
| 4,639,718 | 1/1987 | Gasper | 340/603 |
| 5,578,995 | 11/1996 | Bryant et al. | 340/627 |

Primary Examiner—Jeffery Hofsass
Assistant Examiner—Julie B. Lieu
Attorney, Agent, or Firm—Harry I. Leon; Vivian L. Steadman

[57] ABSTRACT

An improved method and apparatus for monitoring, in real time, the quality of a flowing fluid stream and of automatically taking samples therefrom when the level of particulate matter in the flow stream exceeds an acceptable limit for a predetermined period of time. The apparatus includes a particle monitor and at least one three-way valve electronically linked via a programmable logic controller to the particle monitor. Not only is the latter an instrument for continuously measuring, on-line, numbers known as particle indices which are indicative of particulate matter concentrations in the flow stream, but also the particle monitor generates electronic signals. Both these signals and the particle index are proportional to fluctuations in the intensity of a light beam traversed by particles which are present in a portion of the flow stream during a fixed interval of time. Importantly, the particle monitor can detect relatively short-lived "spikes" in the level of 0.50 micron or larger particles which may be present in the flow stream. Utilizing this sensitivity of the particle monitor to such "spikes", the apparatus can be set to automatically take samples when excursions in the levels of particulate matter occur rather than at random intervals. As a result, the method can facilitate the diagnosis of an impending process equipment breakdown/malfunction in its early stages, while its observable effect is only an infrequent "spike".

3 Claims, 6 Drawing Sheets

Fig_3.

5,798,699

1

METHOD FOR MONITORING AND SELECTIVELY SAMPLING A FLUID FLOW STREAM

BACKGROUND OF THE INVENTION

This invention relates to the monitoring of particulate matter in fluid flow streams and to the collection of samples from such streams for chemical analysis.

Automated samplers which can periodically collect discrete samples of liquid from a fluid flow stream are well known in the prior art. Unless the time interval between sample collections is kept relatively short and the number of samples correspondingly large, major excursions or "spikes" in the levels of contaminants in a flow stream can occur without samples being taken when these levels are elevated. Unfortunately, when such excursions go undetected because of their infrequent occurrence, information can be lost which, if these excursions had been detected earlier, could have prevented a plant shutdown or even catastrophic failure.

On the other hand, discrete batches or samples of a fluid need not actually be collected in order to detect occasional "spikes" in certain contaminants. Specifically, the relative numbers of insoluble particles in a fluid flow stream, even when they occur only as relatively short-lived "spikes", can be measured, on-line, with the use of a particle monitor.

Conveniently, output from the particle monitor, at any given moment of time, can be related to a single number known as the particle index, facilitating data interpretation. To determine each particle index, the particle monitor measures the intensity of a light or infrared radiation beam transmitted through, and perpendicularly to, a suspension flowing through a transparent tube. Fluctuations in the intensity of this beam signal the passage of undissolved material in the flow. From intensity measurements made over a fixed time interval, the particle monitor then computes a ratio equal to the intensity fluctuations, manipulated into a single number, divided by the average intensity of the beam. The particle index for a given time interval is then proportional to the ratio determined for that interval.

In addition to generating particle indices, the particle monitor produces electronic pulses and an analog 4–20 milliamp signal which varies with the particle index and is proportional thereto. Particle monitors which both display the particle index and produce such electronic signals are available commercially. The latter signal, when fed into a suitable controller, can be used to regulate the opening and closing of an electronically-actuated valve. One use of such a valve, according to Bryant and Veal in U.S. Pat. No. 5,578,995, is to selectively dump the entire flow stream from a condensate return system.

As Bryant and Veal also disclosed in the cited patent, a method combining the steps of continuously monitoring particulate matter in a flow stream with a particle monitor and automatically diverting the flow when the measured particle index exceeds a preset value can be used not only to protect process equipment but also to conserve energy and material resources. In a steam condensate return system, for example, this method can be used to eliminate guesswork as to when the condensate flow needs to be dumped and when it can be safely recycled.

Unfortunately, many advantages of this method have gone unrecognized for a long time. Indeed, the usefulness of a particle monitor lies in very high sensitivity to detect particles larger than 0.5 micron in size or larger. Another instrument more sensitive to the presence of the smaller (less than 0.5 micron) insoluble particles—the turbidimeter—has long been considered the instrument of choice for detecting particulate matter in a fluid flow stream. This instrument decreases in sensitivity as particle size increases.

SUMMARY OF THE INVENTION

The object of the present invention is to provide an improved method and apparatus for automatically taking discrete samples during excursions or "spikes" in the levels of insoluble contaminants in a fluid flow stream without having to take samples when these levels are not elevated. Utilization of such a method and apparatus facilitates the collection and analyses of samples only when they are needed, greatly reducing costs.

A still further object of the present invention is to provide means for automatically collecting discrete samples of fluid from a process flow stream so that the fluid can be analyzed for specific contaminants at the earliest stages of process equipment breakdown/malfunction, without necessarily collecting discrete samples prior to such malfunction. Information from the analyses of specific contaminants can then be employed to help identify their source(s) and to pinpoint exactly where problems are occurring in a complex system.

In accordance with the present invention, there is provided an improved method which includes the step of automatically diverting, from its normal course, a portion of a fluid flow stream into a sample container only when the particle index of the fluid has reached a preset level and maintained this level for a predetermined interval of time.

DETAILED DESCRIPTION OF THE INVENTION

Figure 1:
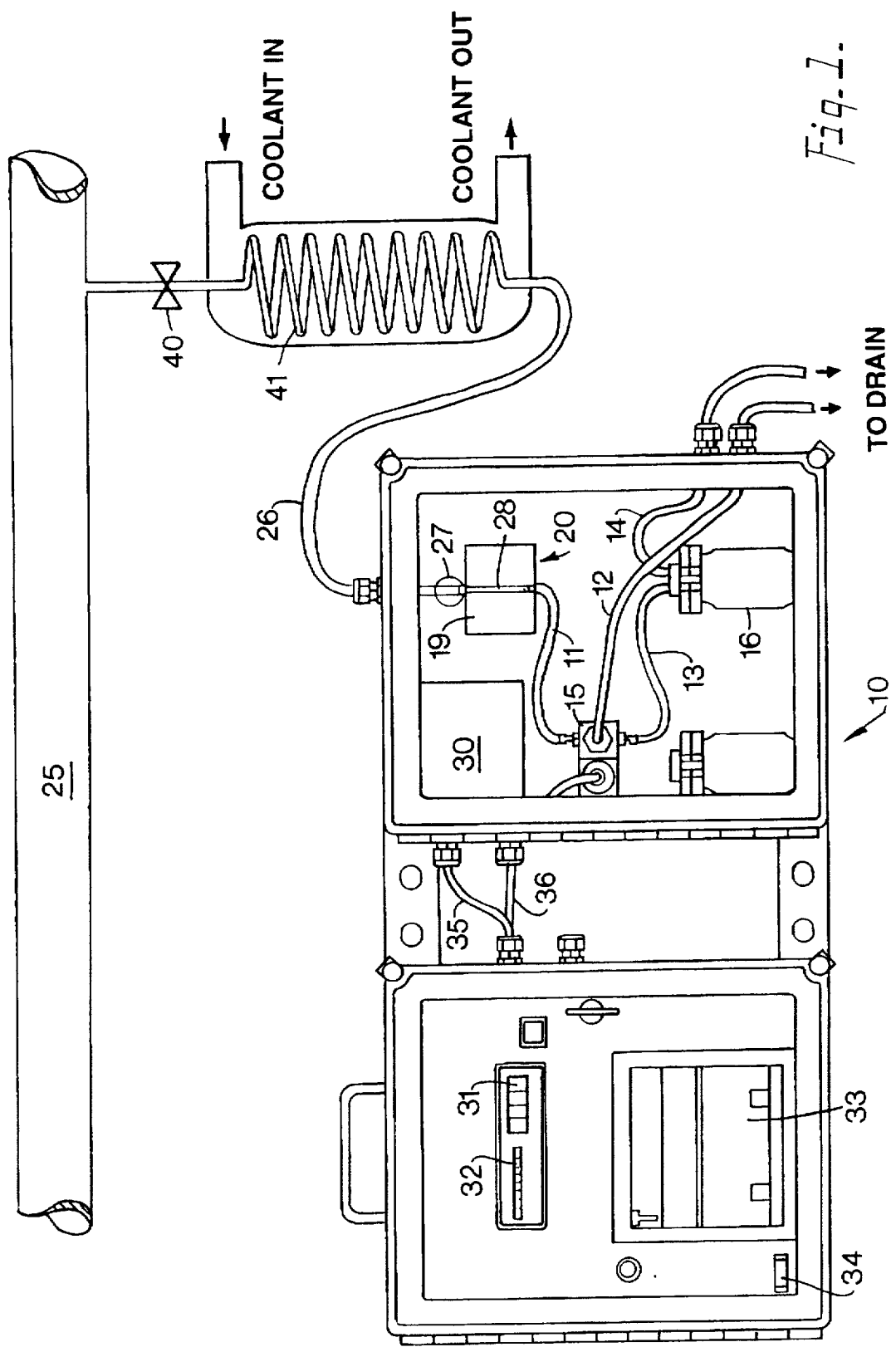
FIG. 1 is a side elevation view, shown partly in schematic, of an apparatus for practicing the method according to the present invention.

The improved method according to the present invention includes the steps of monitoring the level of particulate matter in a clear fluid flow stream and of automatically collecting at least one discrete sample from such a stream during, but only during, each excursion or "spike" in which this level exceeds, for a predetermined time interval, a preset value. Although there are upper limits of particle concentration for which this method is useful, these limits vary widely from one fluid flow stream to another, in part.

because of variances in particle sizes and light absorbing/ reflecting properties between different systems. However, the method was worked satisfactorily when used on raw river water at turbities up to 30 NTU and ultrapure waters with less than one particle per milliliter of 2 micron size.

Referring to the drawings, an apparatus, denoted generally by the reference numeral 10, comprises a 3-way solenoid valve 15, a particle monitor equipped with a sensor 20 which is located upstream of the valve, a controller 24 for electronically actuating the valve, and a power switch 34 common to both the particle monitor and the controller. In use, a small fluid flow stream B is continuously directed through transparent vinyl tubing 26 and into the sensor 20 where both the tubing and flow are intersected by a narrow, but intense beam of radiation B (FIG. 3).

Generated by a light emitting diode (LED) 21, this beam of radiation is preferably about 0.4 mm wide, with a wavelength of about 850 nm, that is, just in the infrared. Only a small fraction (about 20%) of the total flow in the tubing 26 actually passes through the beam. It is assumed that this fraction is representative of the entire flow.

Figure 3:
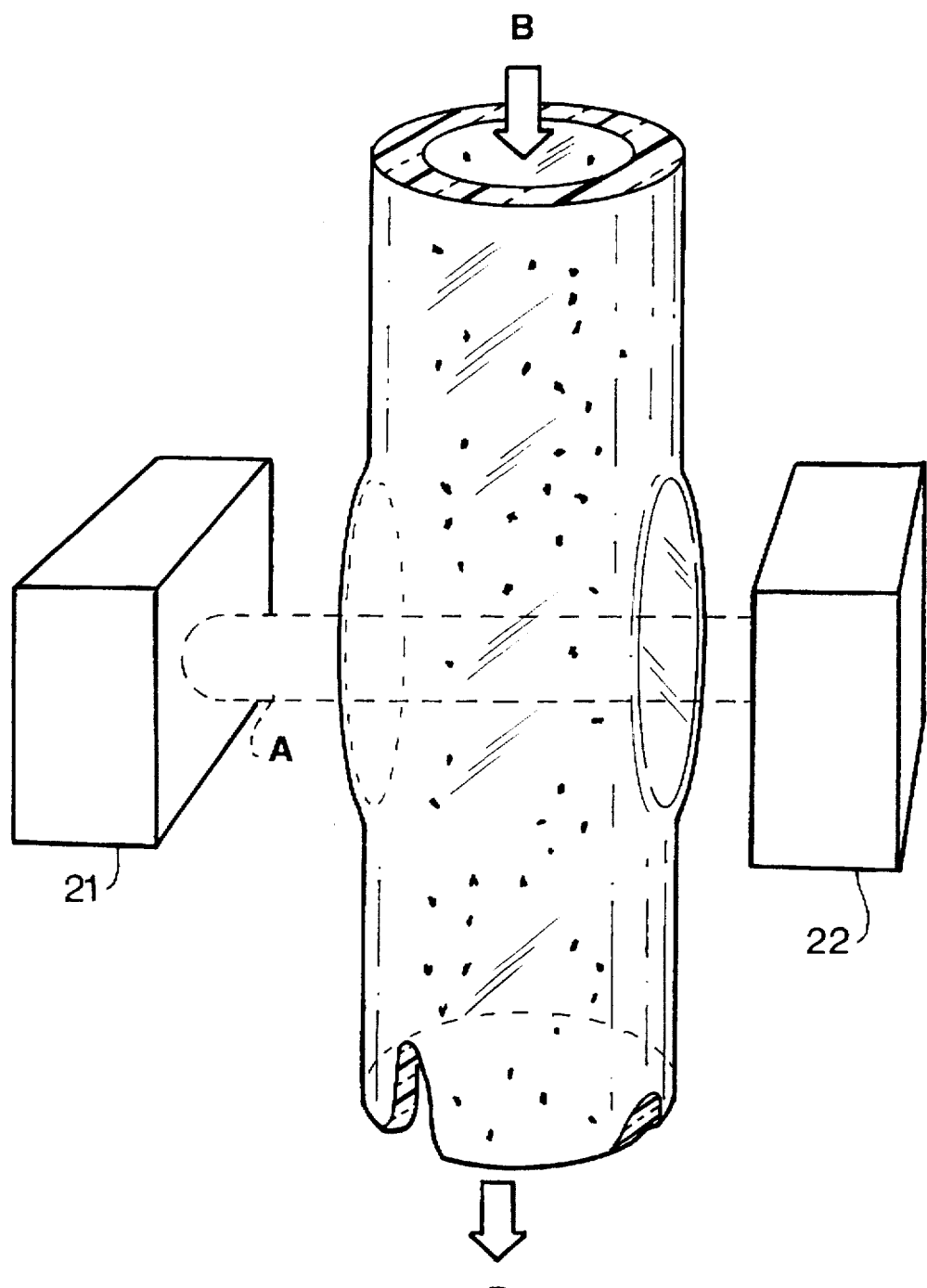
FIG. 3 is a schematic of components within the apparatus according to FIG. 1, the components including sample tubing for transporting a fluid flow stream and both a light emitting diode and a photodetector of a particle monitor, the diode generating a light beam which is partially obscured by particulates in the flow stream as they traverse the light beam.

The transmitted radiation is monitored by a sensitive photodetector 22 (FIG. 3). The latter measures fluctuations in the intensity of the light beam as individual particles pass through it and cast shadows. Changes in these fluctuations indicate changes in the concentrations of insoluble particles present in the flow stream.

Figure 5:
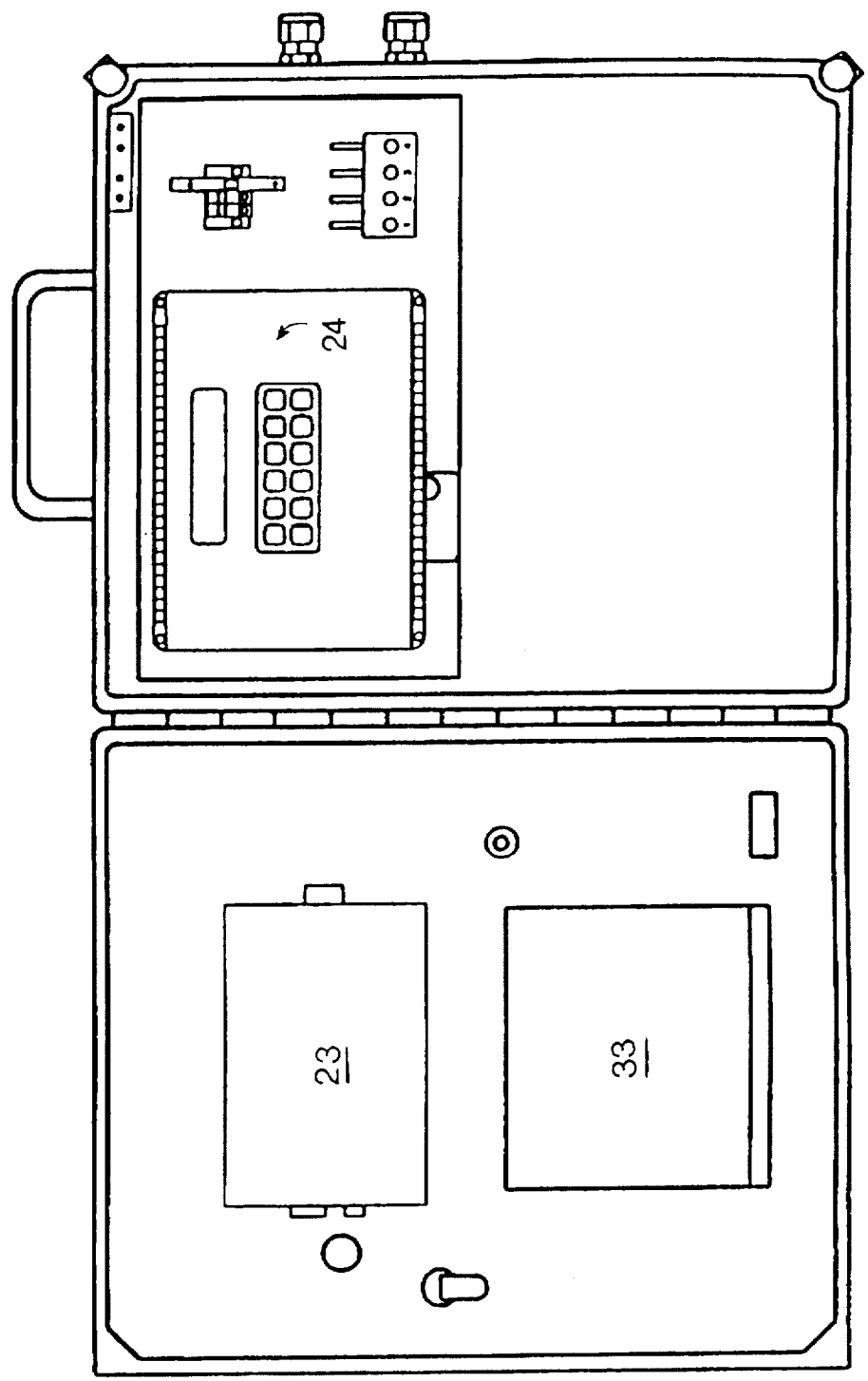
FIG. 5 shows, on an enlarged scale, electronic components including the programmable logic controller within one of the compartments of the apparatus according to FIG. 1.

In addition to the sensor 20, the particle monitor comprises a signal processor, a RMS-DC converter, a voltage-to-frequency (V/F) converter, and a square-wave pulse counter. Preferably, the signal processor, RMS-DC converter, V/F converter, and square-wave pulse counter are all components of a single circuit board 23 (FIG. 5). Upon receiving an electronic signal from the photodetector 22, the board 23 can generate the following outputs: a 4-digit number known as the particle index which is presented on a digital display panel 31, a pulsed output (typically of about 5 Volts in magnitude) recognizable by a microprocessor and a 4–20 milliamp signal.

In the preferred embodiment, each of these outputs is derived from a very small fluctuating component or AC value of the electronic signal from the photodetector 22, which must be separated from a much larger steady component or DC value, a measure of the average transmitted intensity of the beam A (FIG. 3). Separation of the AC signal from the DC is performed by the signal processor. Not only does the signal processor separate the AC signal but also it amplifies the AC value and then passes it to the RMS-DC converter. There the amplified AC signal is converted to a DC voltage equal to its root mean square (RMS) value. From the RMS-DC converter, the RMS signal is then passed to the V/F converter where it is processed into a succession of square-wave pulses whose frequency is proportional to the RMS value. Finally, in the square-wave pulse counter, these pulses are counted over a fixed time interval, in preparation for the pulse count being ultimately presented on the digital display 31 as the particle index.

In this way, each particle index is generated from measurements made continuously over a specific time interval of a fixed length. Experience has indicated that the apparatus 10 performs satisfactorily when the length of the time interval for counting these pulses is set at about 10 seconds. With a time interval of this duration, the various output signals from the particle monitor are smoothed; otherwise, a few very large particles (or bubbles) would momentarily cause the particle index to become very high.

Moreover, in the preferred embodiment, the particle monitor utilizes a sensor 20 with a LED feedback circuit. Such a feedback circuit automatically adjusts the average intensity of the light beam traversing the tubing 26 so that this average intensity is maintained at a constant level at the photodetector 22. Preferably, the DC component is kept constant, by way of example, at 5.7 volts. Alternatively, in the absence of the LED feedback circuit, means for dividing the root mean square of the AC value to produce a ratio must be provided. Each particle index is then proportional to this ratio, a measure of the fluctuations in intensity of the light beam divided by the absolute intensity of the light beam, during a fixed interval of time.

In the preferred embodiment, the particle monitor responds to fluctuations in the intensity of the light beam A, rather than to its absolute intensity, so that the particle monitor is not susceptible to electronic "drift" caused by DC noise, light source variances, optical surface fouling and fogging at elevated temperatures. Changes in the efficiency of the LED or in the transmissivity of the tubing 26, for example, are automatically compensated.

Nevertheless, at some point, the transmissivity of tubing 26 becomes too low; and the tubing must be replaced. To help an operator determine when the tubing 26 must be replaced, the apparatus 10 is preferably equipped with an indicator 32 having a series of LED segments (FIG. 1). As the tubing 26 becomes coated with particles, it transmits less light, causing the diode 21 in the sensor 20 to draw more current. Simultaneously, the indicator 32 responds with more and more illuminated LED segments, a visual reminder of the degree of fouling in the tubing 26.

Figure 2:
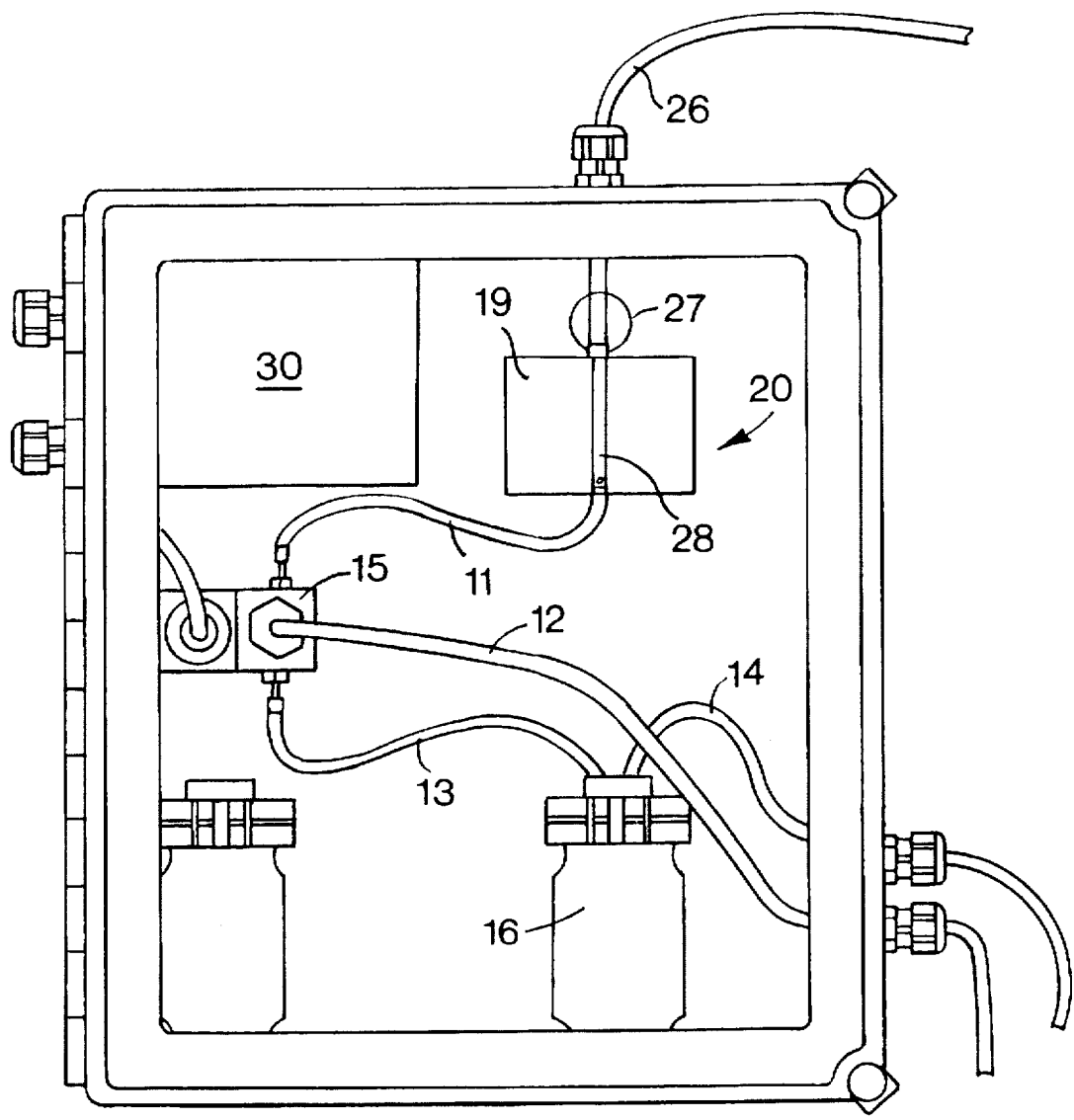
FIG. 2 shows, on an enlarged scale, the sensor in the apparatus according to FIG. 1.

As is best seen in FIG. 2, the sensor 20 includes means for holding a section of the tubing 26 in such as way that this section, which is otherwise round in transverse cross-section, is generally flattened on the sides of the tubing where it is traversed by the light beam, including the sides of the tubing which are proximate with the light source 21 and the photodetector 22, respectively. The flattening of these sides reduces reflection of the light beam from the walls of the tubing 26.

Means for so flattening the tubing 26 includes an elongated pin 28 and a housing 19 for the sensor 20 (FIG. 2). The housing 19 defines an elongated aperture which is approximately rectangular in transverse cross-section and which is sized for receiving both a section of the tubing 26 and the pin 28 in juxtaposed relation. As it is being slideably inserted into the aperture, the pin causes the walls of the tubing section to flatten against three sides of the aperture, as well as against the pin itself. In use, both the tubing section and the pin 28 remain pressed together. When the tubing 26 must be replaced, the pin 28 can be readily removed by grasping a loop 27 affixed thereto (FIG. 2).

A particle monitor which has been found to be satisfactory for this application is the Chemtrac Model PM 3500RSS, available commercially from Chemtrac Systems, Inc. of Norcross, Ga. General specifications for this model are as indicated below:

| | |
|---|---|
| Self Diagnostics | Sample cell tubing LED |
| Sample Cell Type | Flow through |
| Sensor Response Time | Instantaneous |
| Materials Contacting Sample | Clear vinyl |
| Ambient Operating Temperature | 32–120 degrees F. |
| Sample Temperature | 32–120 degrees F. |
| Sample Delay Time (seconds) | 0–3600 |

-continued

| | |
|---|---|
| Sample Time (seconds) | 0–3600 |
| Sample Tubing Size | ⅛ inch I. D., 3/16 inch O. D. |
| Sample Flow Rate | 100–500 ml/min. |
| Sample Flow Control | Constant Head Type |
| Particle Size Range | 1 micron and above |
| Minimum Particle Size Detection | 0.5 micron |
| Particle Index Range | 0–9999 |
| Signal Output | Isolated 4–20 mA (proportional to particle index with adjustable span) 600 ohm load Max |
| Particle Index Readout (Averaging) Interval | 10 seconds |
| Sample Flow Rate | 100–500 ml/min. |
| PLC Reset | Momentary switch (lighted to indicate sample been taken) |
| Recorder | Single pen (standard) |

Simultaneously, as it displays a particle index on the panel 31, the particle monitor generates pulsed output which communicates the same particle index to a microprocessor within the controller 24. Upon receiving this pulsed output, the microprocesssor then compares it with a setpoint known as the "particle index threshold". The latter corresponds to the minimum particle index which the particle monitor must measure in the flow stream before the controller 24 initiates a sequence of events which may result in a sample being collected. Alternatively, the particle monitor can transmit the 4 to 20 milliamp electronic signal to a controller, subject to deadband control. In the latter case, the controller actuates a timer, once the 4 to 20 milliamp signal reaches a level corresponding to an upper setpoint (the particle index threshold), and continues to actuate this timer as long as this signal remains above a lower setpoint (a particle index which in a typical situation measures about 10–20 percent of the particle index threshold). As long as the particle index remains within this deadband, settings on the timer determine the conditions under which an electronic signal can be sent from the controller 24 to the 3-way solenoid valve 15.

In the preferred embodiment, the controller 24 includes a microprocessor with a programmable timer. A suitable controller is the model Z-104 available commercially from Z-World Engineering in Davis, Calif. Upon receiving a signal from the microprocessor that the particle index exceeds the particle index threshold, the programmable timer initially blocks transmission of an electronic signal which would otherwise be sent from the controller 24 to the 3-way solenoid valve 15. With the timer, the controller 24 waits to transmit this signal until the particle index has exceeded the particle index threshold for a predetermined time interval known as the "delta time". Provided the particle index threshold is still met when the "delta time" has expired, the electronic signal from the controller 24 actuates the valve 15, causing its normally open portal to close and its normally closed portal to open. As a result, the flow stream is diverted from tubing section 12 to tubing section 13 fluidly connecting the normally closed portal to the sample container 16 (FIGS. 1 and 2). The timer is also used to block this signal but only after the flow stream has repeatedly flushed the container 16, filling it and the tubing section 13 connecting it to the 3-way solenoid valve 15 before discharging through a tubing section 14 to the drain. Thus overfilling of the container 16 is averted. In the preferred embodiment, the container 16 measures, by way of example, 250 ml in volume and is rinsed at least 3 times before the normally closed portal is closed and a sample is actually collected. A second sample container 16', a duplicate of container 16, is preferably held in reserve (FIG. 2).

As is also illustrated in FIGS. 1 and 2, the 3-way valve 15 is fluidly connected by flexible, transparent tubing 26 to a heat exchanger 41 and indirectly to a process pipe 25. Alternatively, the tubing 26 is fluidly connected directly to the pipe 25. Preferably, the flow rate through the tubing 26, which, by way of example, is 3/16 inch OD vinyl tubing with an internal diameter of 3 mm, is in the range of 100 to 500 ml per minute.

Figure 4:
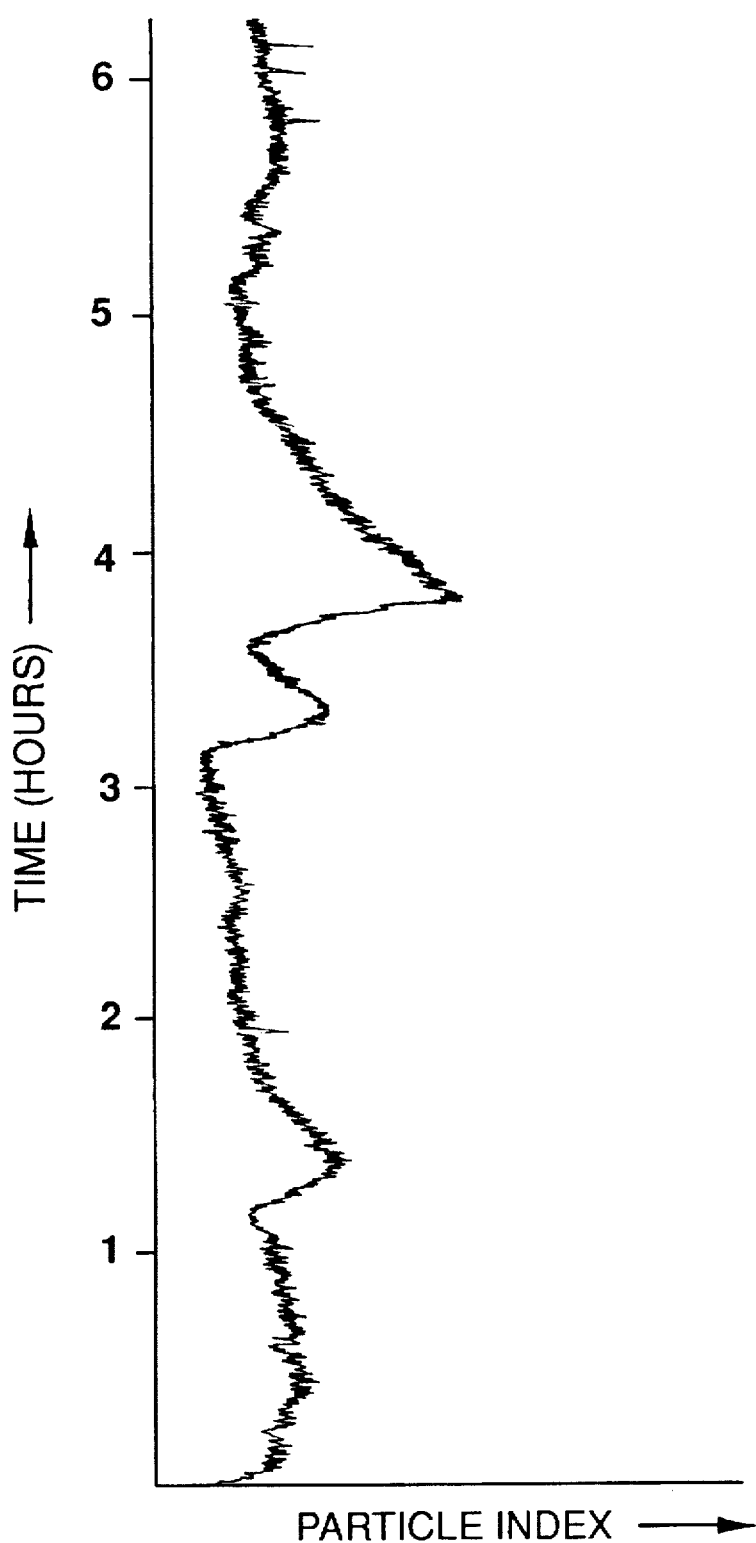
FIG. 4 is a plot of the output of the sensor in an apparatus according to FIG. 1, the plot showing variations in the particle index with time as have been measured in a process flow stream.

In use, determination of a suitable "delta time" for a given fluid flow stream is facilitated by feeding the 4 to 20 milliamp signal from the particle monitor to a strip chart recorder 33 (FIG. 1). As example of a strip chart record generated by a particle monitor monitoring a steam condensate flow stream is shown in FIG. 4; this record reveals three excursions, over a 6 hour period, of the particle index. Each of these excursions lasted at least 15 minutes. However, no excursion was detected by a state-of-the-art turbidimeter which simultaneously monitored the same condensate flow stream over the same time period.

Figure 6:
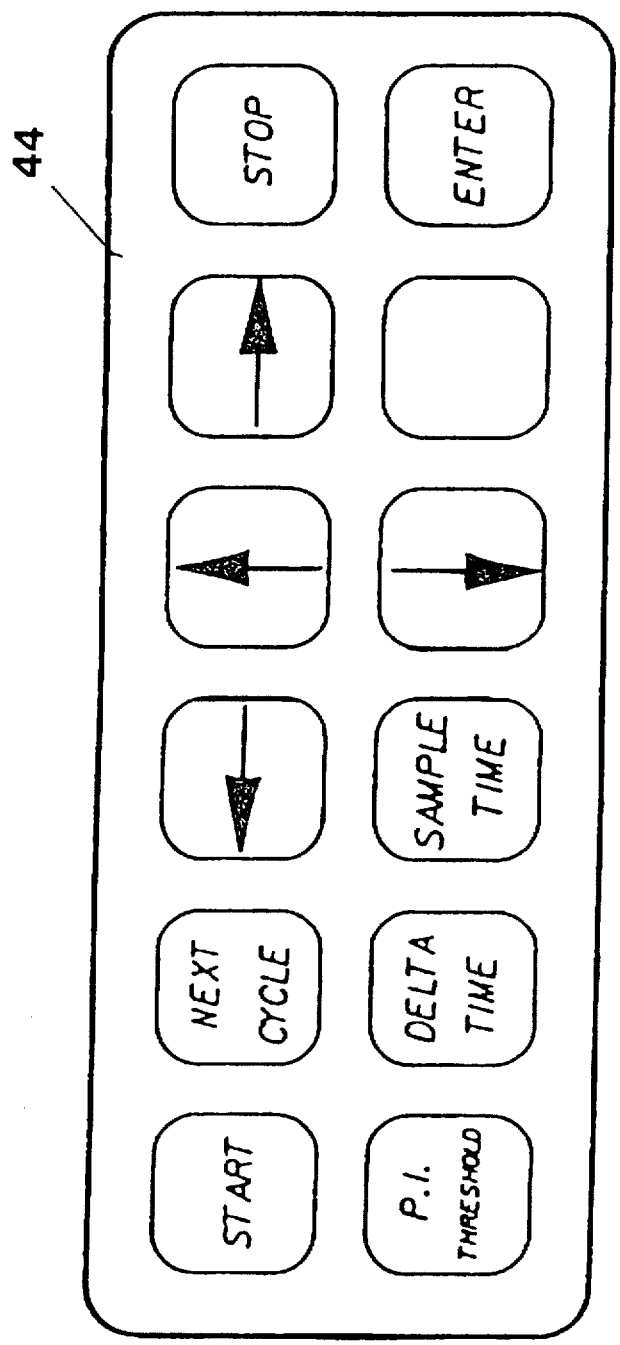
FIG. 6 shows, on a further enlarged scale, a keyboard for the programmable logic controller according to FIG. 5.

Using a strip chart record, such as that shown in FIG. 4, generated by monitoring a particular flow stream, an operator can then make reasonable selections of the "delta time" and of the particle index threshold which can be used to optimize the collection of samples from that stream. The delta time and particle index threshold, once selected, are entered into the memory of the programmable logic controller 24 through its keyboard 44 (FIG. 6).

As the strip chart record shown in FIG. 4 illustrates, the particle monitor can detect relatively short-lived "spikes" of particles which are be present in the flow stream. Utilizing this sensitivity of the particle monitor to detect such "spikes", the apparatus 10 can be set to automatically take samples when excursions in the levels of particulate matter occur rather than at random times. Analysis of individual constituents in such samples can help an operator diagnose an impending process equipment breakdown/malfunction in its early stages, while its observable effect is only an infrequent "spike".

Upstream of the sensor 20, a valve 40, when fully opened, allows flow to pass through the tubing 26 at a maximum rate of 500 ml per minute. The valve 40 comprises means for adjusting the fluid flow rate in the tubing 26 (FIG. 1). This flow rate, however, is not critical as long as it is maintained fairly constant, that is, as long as it stays within about 10 percent of its mean value. Generally, however, higher flows are preferable because they tend to minimize deposit formation on the walls of the tubing 26. Nevertheless, for high flows with high particulate matter content, the particle index may exceed the maximum reading (9999) for the monitor/sampler 10; in such cases, the flow rate must then be lowered accordingly.

Also located upstream of the sensor 20 is a heat exchanger 41 (FIG. 1). With use of the heat exchanger 41, the apparatus can accommodate flows such as steam condensate, hot oils or the like which must be cooled in order to protect the tubing 26. The heat exchanger 41 is used to lower the temperature of such flows to 120 degrees Fahrenheit or less. Moreover, upstream of the heat exchanger 41, tubing which fluidly connects it to the pipe 25 is preferably fabricated from corrosion resistant materials such as stainless steel. The latter are needed to protect surfaces which come into contact with hot fluid.

Optimum performance of the apparatus 10 is obtained by keeping the tubing 26 as short as possible. Indeed, the longer the tubing 26 is, the greater is the likelihood of deposits being formed therein which can restrict flow and/or slough off, causing meaningless, confusing "spikes" in the data. Generally, any erratic phenomena which would appear to the particle monitor within the apparatus 10 to be insoluble particles are to be avoided. In this regard, it is also helpful to locate any flow control devices, except the valve 40, downstream of the sensor 20. Otherwise, if fluid is forced through a pipe constriction or the like, gases can come out of solution as bubbles, interfering with particle index readings.

It is understood that those skilled in the art may conceive other applications, modifications and/or changes in the invention described above. Any such applications, modifications or changes which fall within the purview of the description are intended to be illustrative and not intended to be limitative. The scope of the invention is limited only by the scope of the claims appended hereto.

It is claimed:

1. A method of collecting discrete samples of a fluid flow stream, in which an intense light beam is directed towards a detector and across a portion of the flow stream, each sample of the flow stream being collected only when concentrations of particulate matter in the flow stream exceed a predetermined limiting concentration, comprising:
   (a) continuously measuring, on-line, numbers know as particle indices which are indicative of particulate matter concentrations in the flow stream, each particle index being proportional to a ratio equal to fluctuations in intensity of the light beam divided by absolute intensity of the light beam, the fluctuations being caused by particles which are present in said portion of the flow stream during a fixed interval of time;
   (b) measuring how long the particulate matter concentration continuously exceeds the predetermined limiting concentration;
   (c) comparing each time period over which the particulate matter concentration has been greater than the limiting concentration with a preset time interval; and
   (d) automatically diverting the flow stream into a sample collection container when the particulate matter concentration, as indicated by the particle index, is greater than the predetermined limiting concentration over a time period which is at least as long as the preset time interval.

2. An apparatus for collecting discrete samples of a fluid flow stream, in which an intense light beam is directed towards a detector and across a portion of the flow stream, each sample of the flow stream being collected only when concentrations of particulate matter in the flow stream exceed a predetermined limiting concentration, comprising:
   (a) means for continuously measuring, on-line, numbers known as particle indices which are indicative of particulate matter concentrations in the flow stream, each particle index being proportional to a ratio equal to fluctuations in intensity of the light beam divided by absolute intensity of the light beam, the fluctuations being caused by particles which are present in said portion of the flow during a fixed interval of time; and
   (b) means for automatically collecting at least one sample of the flow stream when the particulate matter concentration, as indicated by the particle index, is greater than the predetermined limiting concentration.

3. The apparatus according to claim 2 wherein the collecting means further comprises means for controlling how long a time period must elapse after the particle index exceeds the predetermined limiting concentration before said sample is taken.

* * * * *